(12) United States Patent
Zedda et al.

(10) Patent No.: US 7,122,663 B2
(45) Date of Patent: Oct. 17, 2006

(54) STABLE FREE NITROXYL RADICALS AS OXIDATION CATALYSTS AND PROCESS FOR OXIDATION

(75) Inventors: Alessandro Zedda, Basel (CH); Massimiliano Sala, Modena (IT); Armin Schneider, Freiburg (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 255 days.

(21) Appl. No.: 10/466,726

(22) PCT Filed: Jan. 15, 2002

(86) PCT No.: PCT/EP02/00340

§ 371 (c)(1), (2), (4) Date: Jul. 18, 2003

(87) PCT Pub. No.: WO02/058844

PCT Pub. Date: Aug. 1, 2002

(65) Prior Publication Data

US 2004/0063932 A1    Apr. 1, 2004

(30) Foreign Application Priority Data

Jan. 23, 2001    (EP)    ................... 01810059

(51) Int. Cl.
*C07D 245/00*    (2006.01)
*C07D 487/00*    (2006.01)
(52) U.S. Cl. .................................... 540/472
(58) Field of Classification Search ............... 540/471, 540/475, 472; 544/198; 562/420, 540; 568/322, 568/403, 436, 485
See application file for complete search history.

(56) References Cited

U.S. PATENT DOCUMENTS

| 4,442,250 A | * | 4/1984 | Cantatore | .................... | 524/98 |
| 5,322,912 A | | 6/1994 | Georges et al. | ............. | 526/204 |
| 6,441,243 B1 | | 8/2002 | Sommerlade et al. | ....... | 568/322 |

FOREIGN PATENT DOCUMENTS

| EP | 1077227 | * | 2/2001 |
| WO | 01/92228 | | 12/2001 |

OTHER PUBLICATIONS

L. Dulog et al., Makromol. Chem. vol. 189, pp. 2611-2615 (1988).

T. Connolly et al., Tetrahedron Letters, vol. 37, No. 28, pp. 4919-4922, (1996).
A. de Nooy et al., Synthesis, "On the Use of Stable Organic Nitroxyl Radicals for the Oxidation of Primary and Secondary Alcohols", Oct. 1, 1996, pp. 1153-1174.
Ciba® CHIMASSORB® 966, "Sterically Hindered Amine Light Stabilizer", Technical Data Sheet, First Ed. Date: Dec. 1989.
M. F. Semmelhack et al., J. Am. Chem. Soc. vol. 106, (1984), pp. 3374-3376.

* cited by examiner

Primary Examiner—Margaret D. Seaman
Assistant Examiner—Niloofar Rahmani
(74) Attorney, Agent, or Firm—Tyler A. Stevenson

(57) ABSTRACT

The instant invention relates to stable free nitroxyl radicals of formula (I)

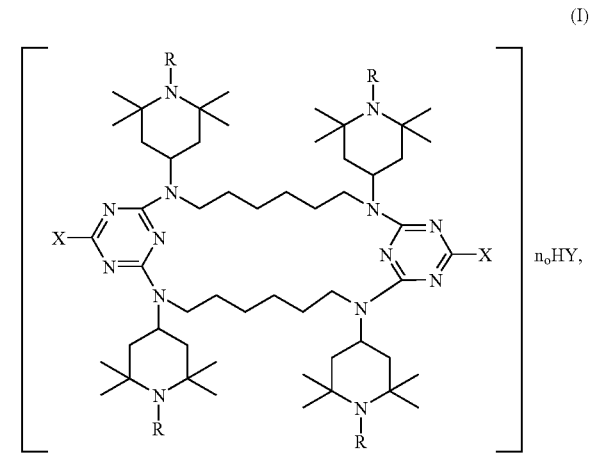

wherein
at least one of the substituents R is —O. and the others are hydrogen or OH;
X is $-NR_1R_2$, wherein $R_1$ and $R_2$ are independently hydrogen, $C_1-C_{18}$alkyl or together with the nitrogen atom to which they are bound form a 5 or 6 membered ring which may be further interrupted by an O atom. Further subjects of the invention are an oxidation process for alcohols to aldehydes or ketones or to carboxylic acids in the presence of a compound of formula (I) and the use of stable free nitroxyl radicals of formula (I) as oxidation catalysts.

3 Claims, No Drawings

STABLE FREE NITROXYL RADICALS AS OXIDATION CATALYSTS AND PROCESS FOR OXIDATION

The instant invention relates to stable free nitroxyl radicals. Stable free nitroxyl radicals are useful for a variety of industrial applications, such as for example as stabilizers to prevent vinyl aromatic monomers from premature polymerization during distillation or purification, as polymerization regulators in controlled radical polymerization processes and as oxidation catalysts in heterogeneous and homogenous oxidation reactions. They are particularly useful as catalysts for the selective oxidation of alcohols to aldehydes or ketones or to carboxylic acids using an alkali hypohalite as oxidizing agent. Consequently an oxidation process and the use of these stable free nitroxyl radicals as oxidation catalysts are also subjects of the invention.

Selectivity is of primary importance in oxidation processes. Further functional groups present in the molecule, such as, for example, double bonds, should generally not be affected under the conditions chosen. Often, the targeted oxidation of secondary alongside primary alcohol functions or vice versa is desired, without the respective other function being affected. In the synthesis of aldehydes from primary alcohols, carboxylic acids are often formed as by-products of the oxidation reaction (over-oxidation), and the oxidation of 1,2-diols or α-hydroxyketones is frequently accompanied by C—C cleavage reactions.

It is known that primary and secondary alcohols can be converted into the corresponding carbonyl compounds using aqueous sodium hypochlorite solution in the presence of catalytic amounts of organic nitroxyl radicals (A. E. J. de Nooy, A. C. Besemer, H. van Bekkum, *Synthesis*, 1996, 1153).

It is also known, that alcohols can be oxidized by Cu(I) and oxygen in the presence of a nitroxyl radical (2,2,6,6-tetramethylpiperidin-1-oxyl, TEMPO). This is for example described by Semmelhack, M. F.; Schmid, Christopher R.; Cortes, David A.; Chou, Chuen S, Oxidation of alcohols to aldehydes with oxygen and cupric ion, mediated by nitrosonium ion in J. Am. Chem. Soc. (1984), 106(11), 3374–6.

Hitherto such reactions—especially when 2,2,6,6-tetramethylpiperidin-1-oxyl (TEMPO) has been used—have predominantly been carried out in homogeneous phase. The reactions were carried out either stoichiometrically or catalytically in respect of TEMPO or the oxidation product resulting therefrom. The working up of the reaction products in such processes often proves to be awkward and involved, since a great deal of effort is required to remove the catalyst and its attendant products.

It has now, surprisingly, been found that specific cyclic oligomeric stable free nitroxyl radicals are ideal catalysts in homogenous and heterogeneous oxidation reactions, which can easily be removed from the reaction products.

Furthermore the instant compounds have high catalytic activity and excellent selectivity.

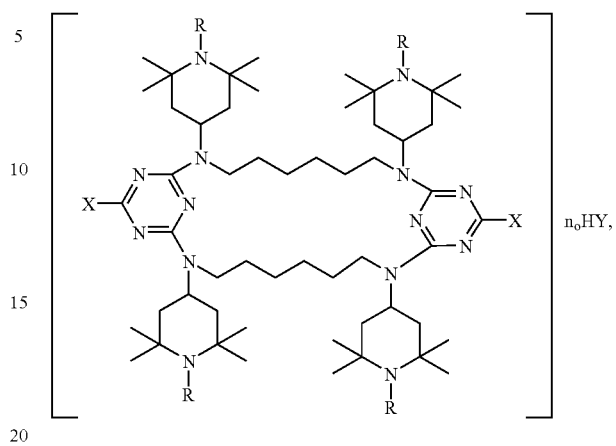

(I)

wherein at least one of the substituents R is –O. and the others are hydrogen or OH;

X is $-NR_1R_2$, wherein $R_1$ and $R_2$ are independently hydrogen, C1–C18alkyl or together with the nitrogen atom to which they are bound form a 5 or 6 membered ring which may be further interrupted by an O atom;

HY is an organic or inorganic acid; and n is 0 or a number from 1–4.

Preferably X is a structural element of formulae

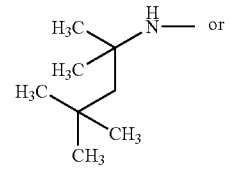

(II)

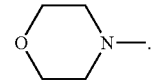

(III)

Most preferably X is of formula (II).

Preferred is a compound of formula (I) wherein at least two of the substituents R are —O•, more preferably 50 to 100% of the substituents R are —O•.

Preferably HY is selected from the group consisting of a halogen containing inorganic protonic acid, a phosphorous containing inorganic acid, a sulfur containing inorganic acid, a $C_1$–$C_4$alkyl carboxylic acid, or a perfluor $C_1$–$C_4$alkyl carboxylic acid or an aromatic carboxylic acid. More preferably HY is HCl, $HClO_4$, HBr, $HPF_6$, $H_3PO_4$, $H_2SO_4$, $CF_3COOH$, $CH_3COOH$, HCOOH or benzoic acid.

Particularly preferred compounds are those wherein n is 0.

The compounds may be prepared from the corresponding amine precursors (R is H) which are for example described in U.S. Pat. No. 4,442,250. When X is of formula (II), the amine precursor is a commercial product, Chimassorb® 966, sold by Ciba Specialty Chemicals.

The oxidation may be carried out in analogy to the oxidation of 4-hydroxy-2,2,6,6-tetramethylpiperidine described in U.S. Pat. No. 5,654,434 with hydrogen peroxide. Another also suitable oxidation process is described in WO 00/40550 using peracetic acid.

As described before the oxidation must not necessarily be carried out until all piperidine nitrogen atoms are oxidized. It can be stopped at many stages before, thus leading to a product mixture which contains NH, NOH and NO• moieties.

A subject of the invention is therefore a process for the selective oxidation of alcohols to ketones or to aldehydes in organic solvents by means of an oxidizing agent, which comprises carrying out the oxidation in the presence of a homogenous or heterogeneous oxidation catalyst of formula (I).

A further subject of the invention is a process for the selective oxidation of alcohols to ketones or to carboxylic acids in aqueous solvents by means of an oxidizing agent, which comprises carrying out the oxidation in the presence of a homogenous or heterogeneous oxidation catalyst of formula (I).

It is one of the advantages that the compound of formula (I) can be protonated by inorganic acids and recovered from organic solvents by washing out with water.

Examples for oxidation agents are oxygen containing organic or inorganic compounds. Typical are organic peracids, such as peracetic acid, $H_2O_2$, hypohalites, halites, halides and oxygen itself or combinations of them.

Preferred is a process for the selective oxidation of alcohols to ketones or to aldehydes or of alcohols to carboxylic acids by means of peracetic acid, $H_2O_2$, hypohalites, halites, halides and oxygen itself or combinations of them, under neutral or alkaline conditions or metal ions like Cu(I), Cu(II), Ru (II), Co(II), Mn(II) and mixtures thereof and oxygen as oxidizing agent, which comprises carrying out the oxidation in the presence of a homogenous or heterogeneous oxidation catalyst of formula (I).

The oxidation catalyst may also be a mixture of compounds of formula (I).

Preferably the oxidation catalyst Is added in an amount of from 0.1 to 20%, more preferably from 0.5% to 10% and most preferably from 0.5 to 5%, by weight, based on the alcohol used.

Generally, a process which comprises carrying out the oxidation by means of an alkali hypohalite under neutral or alkaline conditions is preferred.

Preference is given to a process that uses as the alkali hypohalite LiOCl, NaOCl, KOCl, LiOBr, NaOBr or KOBr.

LiOCl, NaOCl and KOCl are especially preferred, NaOCl being more especially preferred.

The hypohalite, is preferably added in the form of an aqueous solution to the alcohol to be oxidized. The concentration may vary within a wide range and is preferably from 5% to 20% by weight, especially from 10 to 15% by weight, of active chlorine based on the alcohol to be oxidized.

Together with the oxidizing agent, the aqueous solution can be rendered neutral or alkaline by means of a buffer. Preferred buffers are aqueous solutions of alkali or alkaline earth hydroxides, alkali or alkaline earth carbonates and the corresponding hydrogen carbonates and alkali or alkaline earth phosphates and the corresponding hydrogen and dihydrogen phosphates.

Alkali hydrogen carbonates are especially preferred, sodium hydrogen carbonate being more especially preferred.

Preferably the process is carried out at a temperature of less than 30° C., more preferably at a temperature between 5° C. and 20° C.

The pH value of the aqueous oxidation solution after the addition of the desired buffer is in the range from 7 to 12, especially in the range from 8 to 11 and more especially in the range from 8 to 10.

The alcohol to be oxidized may be a monoalcohol, diol or a polyol, monomeric or polymeric like starch or pulp, water soluble or water insoluble or molecules containing other functional groups besides hydroxy.

In the case of liquid alcohols, the reaction can be carried out without the addition of further solvents, but it can be advantageous to carry out the oxidation in a higher dilution.

The compounds of formula (I) may also be used as polymerization regulators in controlled free radical polymerization, as for example described in U.S. Pat. No. 5,322,912, as polymerization inhibitors during distillation or purification of vinyl aromatic monomers or as flame retardants.

PREPARATION EXAMPLES

Example 1

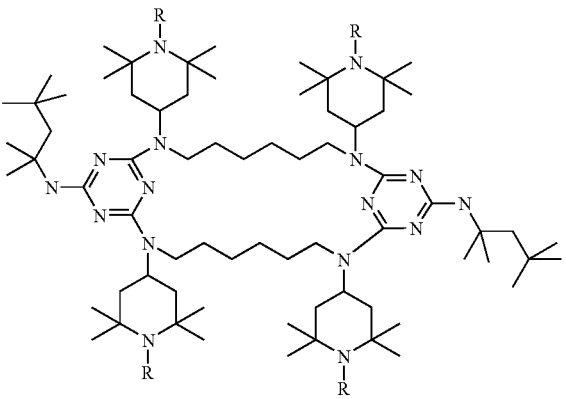

R=H, O. at least one is O.

In a 500 ml three necked flask 50 gr of CHIMASSORB® 966, toluene 250 ml, and 42 g of potassium carbonate were added. The heterogeneous mixture was cooled at 5–10° C. and with vigorous stirring 72.5 g of a solution of peracetic acid (35%) in acetic acid was added slowly over about 1 h. The reaction mixture was allowed to stand for 2 h at 5–10° C. and 10 g of potassium carbonate were added; after that the temperature was spontaneously allowed to rise to 25° C. and the reaction was continued for additional 2 h at 25–30° C.; after that the temperature was increased until to 500C and maintained for 1 h. The mixture was then concentrated under reduced pressure and the crude product was washed with water and dried under vacuum. 44 g of the desired rose-coloured product was obtained. In order to increase the purity of the nitroxyl product, the crystallization of unreacted CHIMASSORB ® 966 has been repeated four times in dichloromethane The organic layer has then concentrated and dried under vacuum; obtaining a rose coloured solid having the following analytical data:

Melting range: 267–270° C.
Nitroxyl Yield by ESR: 95%

Example 2

In a flask 1 g of the product from example 1 was added to 100 g of a 37% solution of hydrochloric acid in water. The mixture was stirred for 8 hours at room temperature, until a homogeneous yellow-coloured solution was obtained. The water was evaporated and the remaining salt was dried under vacuum.

EXAMPLES FOR THE USE AS CATALYST IN OXIDATION REACTIONS

Example A

Use as Homogeneous Catalyst for Alcohol Oxidation in Organic Solvents

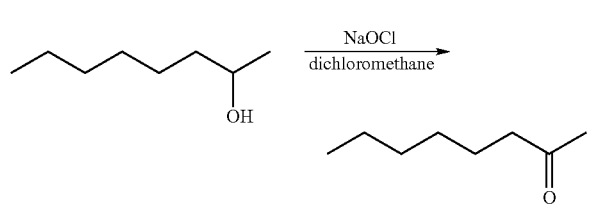

In a flask 0.072 g (0.05 mmol) of the product from example 1, 2.5 g (19.2 mmol) of 2-octanol and 10 ml of dichloromethane and 2.8 gr of KHCO3 (20% sol.) were added; the heterogeneous mixture was cooled to 10–15° C. then was dropped 13.8 g of an aqueous solution of NaOCl (10.5%). After 3 hours the crude organic layer was analyzed using GC: 98.6% of 2-octanone was obtained as desired product.

Example B

Recovery of the Catalyst

The organic layer of the reaction mixture in Example A was separated from the aqueous phase and stirred with 10 ml of concentrated HCl (37% in water). After 30 minutes the colorless organic layer was separated from the slightly yellow colored aqueous phase. The water was evaporated and the separated salt of the catalyst was dried under vacuum.

Example C

Use as Heterogeneous Catalyst for Alcohol Oxidation in Organic Solvents

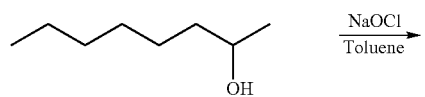

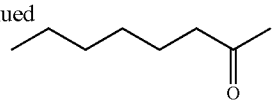

In a flask 0.072 g (0.05 mmol) of the product from example 1, 2.5 g (19.2 mmol) of 2-octanol, 10 ml of toluene and 2.8 gr of KHCO3 (20% sol.) were added; the heterogeneous mixture was cooled to 10–15° C. then were added 13.2 g of an aqueous solution of NaOCl (10.5%). After 2 hours the crude organic layer was analyzed using GC and $^1$H-$^{13}$C-NMR and 100% of 2-octanone was obtained as desired product. The catalyst was recovered by filtration of the crude reaction mixture.

Example D

Use as Heterogeneous Catalyst for the Selective Oxidation of Primary Alcohols in Organic Solvents

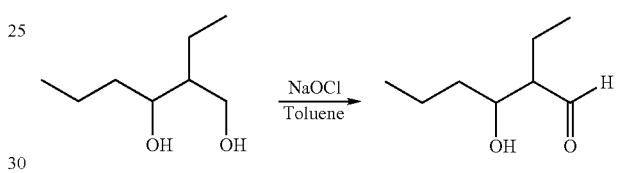

In a flask 0.06 g (0.042 mmol) of the product from example 1, 2.5 g (17.1 mmol) of 2-ethyl-1,3-hexane-diol and 10 ml of toluene were added; the heterogeneous mixture was cooled to 10–15° C. then was dropped 9.8 g of an aqueous solution of NaOCl (13%) maintaining the pH between 8.5–9.5 using a water solution of NaHCO$_3$. After 2 hours the crude organic layer was analyzed using GC and $^1$H-$^{13}$C-NMR and 77% of 2-ethyls 3-hydroxy-hexanal was obtained as desired product. The catalyst was recovered by filtration of the crude reaction mixture.

Example E

Use as Heterogeneous Catalyst for the Oxidation of Alcohols in Water

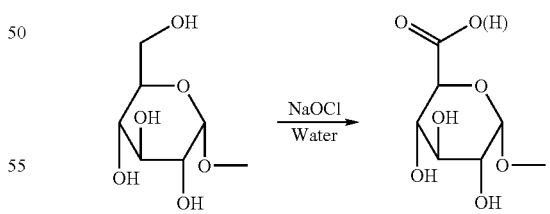

In a flask 0.02 g (0.014 mmol) of the product from example 1, 0.195 g (1.0 mmol) of methyl-α-D-glucopyranoside and 10 ml of water were added; the mixture was kept at room temperature then was dropped 8 ml of an aqueous solution of NaOCl (0.5M) maintaining the pH at 9.5 using a 0.12 M solution of NaOH. After 24 hours the crude organic layer was analyzed using HPLC. 96% of the carboxy acid was obtained as desired product. The catalyst was recovered by filtration of the crude reaction mixture.

Example E

Use as Homogeneous Catalyst for the Oxidation of Alcohols in Water

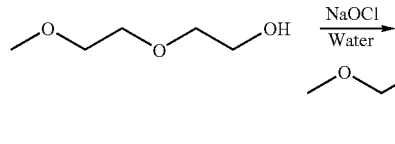

In a flask 0.30 g (0.2 mmol) of the product from Example 2, 2.5 g (20.8 mmol) of diethyleneglycolmonomethylether and 10 ml of water were added; the mixture was cooled to 10–15° C. then was dropped 48 g of an aqueous solution of NaOCl (13%) maintaining the pH between 6–7 using a water solution of $KH_2PO_4$ After 4 hours the crude solution was analyzed using GC and $^1H$— and $^{13}C$-NMR. 95% of the carboxy acid was obtained as desired product. The catalyst was recovered by precipitation at pH>8 and filtration of the reaction mixture.

Example F

Use as Catalyst for the Oxidation of Alcohols in Absence of Solvent

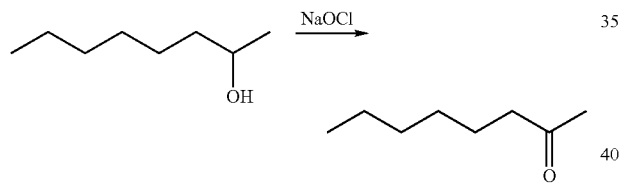

In a flask 125 µl (0.8 mmol) of the 2-octanol, 3.2 mg (8 µmol) of the product from example 1 and 2.86 ml NaOCl-solution (0.35M; 1.0 mmol; pH 9.1 with $KHCO_3$) were added; the mixture was maintained at room temperature under vigorously stirring. After one hour the crude organic layer was analyzed using GC: 100% of 2-octanone was obtained as desired product. The catalyst was recovered by filtration of the crude reaction mixture.

What is claimed is:

1. A compound of formula (I)

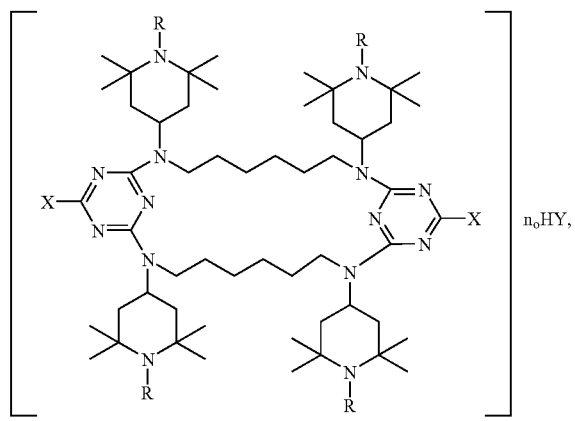

wherein
at least one of the substituents R is —O• and the others are hydrogen or OH;
X is —$NR_1R_2$, wherein $R_1$ and $R_2$ are independently hydrogen, $C_1$–$C_{18}$alkyl or together with the nitrogen atom to which they are bound form a 5 or 6 membered ring which may be further interrupted by an O atom;
HY is an organic or inorganic acid; and
n is 0 or a number from 1 –4.

2. A compound according to claim 1 wherein X is a structural element of formulae

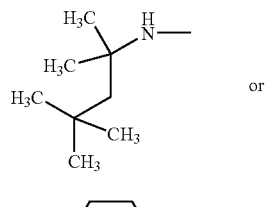

or

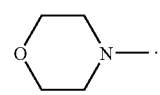

3. A compound according to claim 1 wherein n is 0 and at least two of the substituents R are —O•.

* * * * *